United States Patent
Wendlinger

(10) Patent No.: US 9,884,797 B2
(45) Date of Patent: Feb. 6, 2018

(54) PROCESS FOR THE PREPARATION OF 1-CHLORO-2,2-DIFLUOROETHANE

(71) Applicant: Arkema France, Colombes (FR)

(72) Inventor: Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 15/533,406

(22) PCT Filed: Dec. 11, 2014

(86) PCT No.: PCT/IB2014/003048
§ 371 (c)(1),
(2) Date: Jun. 6, 2017

(87) PCT Pub. No.: WO2016/092340
PCT Pub. Date: Jun. 16, 2016

(65) Prior Publication Data
US 2017/0327442 A1    Nov. 16, 2017

(51) Int. Cl.
C07C 17/354    (2006.01)
C07C 17/25    (2006.01)
C07C 17/38    (2006.01)

(52) U.S. Cl.
CPC ............ *C07C 17/354* (2013.01); *C07C 17/25* (2013.01); *C07C 17/38* (2013.01)

(58) Field of Classification Search
CPC ...... C07C 17/354; C07C 17/357; C07C 17/25
See application file for complete search history.

(56) References Cited

FOREIGN PATENT DOCUMENTS

WO    WO-2013/053800    4/2013

OTHER PUBLICATIONS

International Search Report dated Aug. 18, 2015 for PCT/IB2014/003048.

*Primary Examiner* — Jafar Parsa
(74) *Attorney, Agent, or Firm* — Brinks Gilson & Lione

(57) ABSTRACT

The present invention provides a process for the preparation of 1-chloro-2,2-difluoroethane comprising the following stages: (i) dehydrofluorinating 1,1,1-trifluoro-2-chloroethane to form a product stream comprising 1-chloro-2,2-difluoroethylene, optionally separation of 1-chloro-2,2-difluoroethylene from the product stream and (ii) hydrogenating 1-chloro-2,2-difluoroethylene obtained in stage (i) to give 1-chloro-2,2-difluoroethane.

16 Claims, No Drawings

PROCESS FOR THE PREPARATION OF 1-CHLORO-2,2-DIFLUOROETHANE

CROSS-REFERENCE TO RELATED APPLICATIONS

This application is a U.S. National Stage application of International Application No. PCT/IB2014/003048, filed Dec. 11, 2014.

The present invention relates to a process for the manufacture of 1-chloro-2,2-difluoroethane (HCFC-142) from 1,1,1-trifluoro-2-chloroethane (HCFC-133a).

HCFC-142 is a known foam blowing agent and can also be employed as a starting material in the preparation of agrochemicals or pharmaceuticals.

Several methods of preparing HCFC-142 from chlorinated organic raw materials are known. For example, FR 2 783 820 describes a process for the manufacture of HCFC-142 using a liquid phase reaction between hydrogen fluoride (HF) and 1,1,2-trichloroethane (HCC-140). The reaction is carried out at 30° C. to 180° C. in the presence of a Lewis acid containing Sn, Sb, Ta, Nb or Ti.

US 2002/0183569 discloses a process for the manufacture of HCFC-142 using a catalytic gas phase reaction between HCC-140 and hydrogen fluoride, wherein the catalyst is typically one or more supported or unsupported fluorinated salts of an element chosen from of chromium, iron, niobium, nickel, antimony, tin, tantalum and titanium.

WO 2013/053800 relates to a catalytic gas phase fluorination of HCC-140 and/or 1,2-dichloroethene (HCC-1130), using HF and a specific catalyst prepared by co-depositing $FeCl_3$ and $MgCl_2$ on chromia-alumina, or $Cr(NO_3)_3$ and $Ni(NO_3)_2$ on active carbon, or by doping alumina with $ZnCl_2$.

The inconvenience with the processes mentioned above, is that they use chlorinated raw materials which are not readily available.

It has now been discovered that HCFC-142 can conveniently be prepared with high yield and selectivity from HCFC-133a, a readily available raw material.

SUMMARY

The present invention provides a process for the preparation of HCFC-142 comprising the following stages:
(i) dehydrofluorinating HCFC-133a to give a product stream comprising HCC-1122,
(ii) hydrogenating the HCC-1122 obtained in the preceding stage to give HCFC-142.

DETAILED DESCRIPTION OF EMBODIMENTS

The process of the invention comprises dehydrofluorination and hydrogenation reactions where, according to one embodiment, the product stream from the first reaction forms the feedstock for the second reaction, and according to another embodiment, the product stream from the first reaction is subject to a separation stage before being fed into the second reaction.

The reactions can be carried out continuously, semi-continuously or batch wise. Thus the invention offers an efficient and economical process for preparing HCFC-142 from a readily available and inexpensive starting material, HCFC-133a.

The present invention provides thus a process for the preparation of 1-chloro-2,2-difluoroethane comprising the following stages: (i) dehydrofluorinating 1,1,1-trifluoro-2-chloroethane to form a product stream comprising 1-chloro-2,2-difluoroethylene, optionally separation of 1-chloro-2,2-difluoroethylene from the product stream and (ii) hydrogenating 1-chloro-2,2-difluoroethylene obtained in stage (i) to give 1-chloro-2,2-difluoroethane.

The dehydrofluorination reaction of stage (i) can be performed in any conventional manner, for example in either the liquid or gas phase, and the operating conditions may be selected so that the reactions are substantially quantitative.

Therefore, while the preferred embodiments of the invention involve contacting HCFC-133a with a dehydrofluorinating agent, the latter is not fundamental in order to realize the invention.

In one preferred embodiment, the dehydrofluorinating agent is a base.

Suitable bases include metal hydroxides, and particularly basic metal hydroxides, such as alkali or alkaline earth metal hydroxides.

The term "alkali metal hydroxide" refers to a compound or mixture of compounds selected from lithium hydroxide, sodium hydroxide, potassium hydroxide, rubidium hydroxide and caesium hydroxide.

The term "alkaline earth metal hydroxide" refers to a compound or mixture of compounds selected from beryllium hydroxide, magnesium hydroxide, calcium hydroxide, strontium hydroxide and barium hydroxide.

Especially preferred base dehydrofluorinating agents are selected from lithium hydroxide, sodium hydroxide, potassium hydroxide, magnesium hydroxide, and calcium hydroxide.

Dehydrofluorination with one of the aforementioned base dehydrofluorinating agents may be conducted in the approximate temperature range from 20° C. to 300° C., preferably from 50° C. to 250° C., and more preferably from 80° C. to 200° C.

A suitable absolute pressure is in the approximate range from 0.1 to 30 bar.

The base dehydrofluorinating agent is typically present to the extent of 1 to 90% by weight (% wt.) with respect to all compounds present in stage (i), preferably, from 2 to 85% wt., and advantageously from 5 to 65% wt.

The duration of base dehydrofluorination reaction may vary, but is suitably in the range from 30 seconds to 50 hours, preferably in the range from 10 minutes to 30 hours, and advantageously in the range from 1 to 20 hours.

Dehydrofluorination may be carried out in the presence or absence of a solvent.

If no solvent is used, HCFC-133a may be passed over a solid dehydrofluorinating agent, or into or over a semi-solid (molten) dehydrofluorinating agent.

If a solvent is used, in certain embodiments a preferred solvent is water, while in others, alcoholic solvents such as alcohols (e.g. propan-1-ol), diols (e.g. ethylene glycol) and polyols (e.g. polyethylene glycol) may be preferred. In further embodiments, solvents from the class known as polar aprotic solvents may be preferred. Examples of such polar aprotic solvents include diglyme, sulfolane, dimethylformamide (DMF), dioxane, acetonitrile, hexamethylphosphoramide (HMPA), dimethyl sulphoxide (DMSO) and N-methyl pyrrolidone (NMP). Solvents can be used alone or in combination. The boiling point of the solvent is ideally such that it does not generate excessive pressure under set reaction conditions.

Dehydrofluorination may preferably employ water as solvent and thus occur, for example, in an aqueous solution of at least one base, such as an alkali or alkaline earth metal hydroxide, without the need for a co-solvent or diluent.

However, a co-solvent or diluent can also be used, in various embodiments of the invention, for example to modify the system viscosity, to act as a preferred phase for reaction by-products, or to increase thermal mass. Useful co-solvents or diluents may be those that do not affect or negatively impact the equilibrium and kinetics of the process, including alcohols such as methanol and ethanol; diols such as ethylene glycol; ethers such as diethyl ether or dibutyl ether; esters such as methyl acetate, ethyl acetate and the like; linear, branched or cyclic alkanes such as cyclohexane, methylcyclohexane; fluorinated diluents such as hexafluoroisopropanol, perfluorotetrahydrofuran and perfluorodecalin.

The base mediated dehydrofluorination reaction as described above is optionally catalysed. The catalyst is ideally a phase transfer catalyst which facilitates the transfer of ionic compounds into an organic phase from, for example, a water phase. If water is used as solvent, an aqueous or inorganic phase is present as a consequence of the alkali metal hydroxide and an organic phase is present as a result of the fluorocarbon. The phase transfer catalyst facilitates the reaction of these dissimilar components. While different phase transfer catalysts may function in different ways, their mechanism of action does not determine their utility in the present invention, provided that they facilitate the dehydrofluorination reaction.

The phase transfer catalyst can be ionic or neutral and is typically selected from a group chosen from crown ethers, onium salts, cryptands, and polyalkylene glycols and derivatives thereof (e.g. fluorinated derivatives thereof).

An effective amount of the phase transfer catalyst may be used in order to effect the desired reaction, influence selectivity to the desired products, or enhance the yield; such an amount can be determined by limited experimentation once the reactants, process conditions and phase transfer catalyst are selected. Typically, the amount of catalyst used relative to the amount of organic compounds present is from 0.001 to 20 mol %, such as from 0.01 to 10 mol %, or for example from 0.05 to 5 mol %.

Combinations of phase transfer catalysts from within one of the groups cited above may also be useful as well as combinations or mixtures from more than one group. Crown ethers and quaternary ammonium salts are the currently preferred groups of catalysts, for example 18-crown-6 and its fluorinated derivatives and benzyltriethylammonium chloride.

In another preferred embodiment, dehydrofluorination of HCFC-133a is carried out using a dehydrofluorination catalyst as dehydrofluorinating agent.

The dehydrofluorination catalyst may be based on a metal, and ideally a transition metal or an oxide, halide or oxyhalide derivative thereof. Suitable catalysts therefore include iron chloride, chromium oxyfluoride, nickel (including Ni mesh lattices), nickel chloride, chromium fluoride, and mixtures thereof. Other possible catalysts are catalysts supported on charcoal, antimony-based catalysts, aluminium-based catalysts (such as aluminium fluoride, aluminium oxide, aluminium oxyfluoride, fluorinated alumina), palladium, platinum, rhodium and ruthenium. Reference may be made to the list given in document U.S. Pat. No. 5,396,000, column 1, line 50 to column 2, line 2 or to the list given in WO 2007/056194, page 16, lines 13-23.

In one embodiment, a mixed catalyst containing both chromium and nickel is used. The Cr:Ni mole ratio is generally between 0.5 and 5, for example between 0.7 and 2, and more particularly approximately equal to 1. The catalyst may contain, by weight, from 0.5% to 20% chromium and from 0.5% to 20% nickel, and preferably from 2 to 10% of each.

The metal may be present in metallic form or as a derivative thereof, such as an oxide, halide, or oxyhalide, generally obtained via activation of the catalytic metal. Although activation of the metal is not necessary, it is preferred.

Mixed catalysts may comprise chromium and nickel in activated or inactivated form, optionally on a support that may have undergone activation of the metal therein.

Catalysts may preferably be supported using an aluminium based support such as alumina, activated alumina or aluminium derivatives. Aluminium derivatives are especially aluminium halides or oxyhalides, described for example in U.S. Pat. No. 4,902,838, or obtained via the activation process described below.

The catalyst may be prepared by impregnating a catalyst support based on alumina, more particularly "activated" alumina of high porosity, and which is different from alumina that has undergone metal activation treatment. In a first stage, the alumina is transformed into aluminium fluoride or into a mixture of aluminium fluoride and alumina, by fluorination using air and hydrofluoric acid. The degree of conversion of alumina into aluminium fluoride depends mainly on the temperature at which the alumina is fluorinated, which is generally between 200° C. and 450° C. and preferably between 250° C. and 400° C. The support is then impregnated using aqueous solutions of chromium and nickel salts or using aqueous solutions of chromic acid, nickel salt and methanol, the latter serving as a chromium-reducing agent. The chromium and nickel salts that may be used include the chlorides of these metals or others such as oxalates, formates, acetates, nitrates, sulfates, and nickel dichromate, provided that these salts are soluble in the amount of water that may be absorbed by the support. The catalyst may also be prepared via direct impregnation of alumina (generally activated) using solutions of the chromium and nickel compounds mentioned above. In this case, at least partial conversion (i.e. 70% or more) of the alumina into aluminium fluoride or aluminium oxyfluoride occurs during activation of the catalyst metal.

Activated aluminas that are suitable for the preparation of the catalyst are well-known and commercially available. They are generally prepared by calcination of alumina hydrates (i.e. aluminium hydroxides) at a temperature of between 300° C. and 800° C. Whether or not they are activated, the aluminas may contain large amounts, for example up to 1000 ppm, of sodium without this hindering catalytic performance.

Preferably, but not necessarily, the catalyst is "conditioned" or "activated". These terms are used synonymously to indicate that the catalyst is converted into constituents that are active and stable under the required reaction conditions via a preliminary activation operation before use. Activation may be performed either "in situ" in the dehydrofluorination reactor or in suitable apparatus designed to withstand the activation conditions.

Activation generally comprises the following stages:

A drying stage. This drying stage is performed at high temperature (250° C. to 450° C., preferably 300° C. to 350° C.) usually under a stream of nitrogen or air, optionally preceded by an initial drying stage at low temperature (100° C. to 150° C., preferably 110° C. to 120° C.) in the presence of air or nitrogen. The total duration of the drying stage may be between 10 and 50 hours.

A fluorination stage performed at low temperature (180° C. to 350° C.) using a mixture of hydrofluoric acid and nitrogen, while controlling the HF content so that the temperature does not exceed 350° C. The duration of the fluorination stage may be between 10 and 50 hours.

An optional finishing stage under a stream of pure hydrofluoric acid or hydrofluoric acid diluted with nitrogen, at a temperature of up to 450° C. The duration of the finishing stage may be between 2 and 15 hours.

During the operation, catalytic precursors (for example nickel and chromium halides, nickel chromate or dichromate, chromium oxide) are converted into corresponding fluorides and/or oxyfluorides, resulting in a release of water and/or of hydrochloric acid. Chemical analysis of certain elements (i.e. chromium, nickel, fluorine, aluminium, oxygen) following activation allows the mineral composition of the catalyst to be characterized. One such catalyst is described in EP-A-486 333 (page 3, lines 11-48; Examples 1A, 2A and 4A).

Dehydrofluorination stages using a catalyst as dehydrofluorinating agent may be performed at temperatures of between 150° C. and 650° C., preferably between 200° C. and 600° C., advantageously between 250° C. and 550° C., and particularly advantageously between 300 and 500° C.

The contact time (ratio between the volume of catalyst and the total charge flow) is generally between 0.1 and 100 seconds, preferably between 1 and 50 seconds and advantageously between 5 and 40 seconds.

The reaction pressure for the dehydrofluorination reaction using a dehydrofluorination catalyst may be atmospheric, sub-atmospheric, or superatmospheric.

The reaction of stage (i) may be performed in one or more reactors designed to house reactions involving halogens. Such reactors are known to those skilled in the art, and may have linings based on Hastelloy®, Inconel®, Monel® or fluoropolymers, for example. If necessary, the reactor may also comprise heat-exchange means.

The catalyst may also be regenerated after a certain period of time in order to restore its activity, using any conventional means in the art, for example by treatment with an oxidizing agent or with hydrogen fluoride.

If stage (i) is carried out in the gas phase, a diluent gas such as nitrogen, helium or argon may be used in the reaction, with nitrogen being a preferred inert gas. The process may also be carried out in the presence of a gaseous oxidizing agent in order to oxidize any carbonaceous deposits into $CO_2$ gas. For this purpose, one might use for example, an oxygen containing gas such as air. It may be preferred to use a gaseous oxidizing agent over an inert gas, since it can extend the lifetime of the catalyst.

Any dehydrofluorinating agent used in stage (i) may preferably be recovered after this stage of the process.

While the use of a dehydrofluorinating agent is sometimes preferred, it is not required.

Another preferred way of carrying out the dehydrofluorination of 1,1,1-trifluoro-2-chloroethane (HCFC-133a) is via thermal decomposition in a reaction zone at elevated temperature in the absence of a dehydrofluorinating agent. Appropriate temperatures range from 350° C. to 1000° C., and advantageously between 450° C. and 900° C. The residence time of gases in the reaction zone is generally between 0.1 and 100 seconds, preferably between 1 and 50 seconds and advantageously between 2 and 40 seconds.

The reaction pressure for the dehydrofluorination reaction at elevated temperature in the absence of catalyst may be atmospheric, sub-atmospheric or super-atmospheric. Generally, near atmospheric pressures are preferred. However, the dehydrofluorination can be beneficially run under reduced pressure (i.e. pressures of less than one atmosphere).

Thermal decomposition may optionally be carried out in the presence of an inert gas such as nitrogen, helium or argon, in order to increase the extent of dehydrofluorination. Nitrogen is the preferred inert gas.

The reaction is performed in the same type of reactor as for the other dehydrofluorination embodiments. Optionally, the reactors may be packed with the metal in a suitable form, such as particles or formed shapes including perforated plates, rings, wire, screen, chips, pipe, shot, gauze, or wool.

The hydrogenation stage may also be performed in a conventional manner for a person skilled in the art, in the gas phase, preferably using a catalyst. A person skilled in the art may select the operating conditions so that the reactions are substantially quantitative.

Catalysts that may be used in the hydrogenation reaction include those that are already known for this purpose. Mention may be made especially of catalysts based on a group VIII metal or rhenium. This catalyst may be supported (for example on charcoal, alumina, aluminium fluoride, and so on) or unsupported (for instance Raney nickel). Suitable metals include platinum and palladium, advantageously supported on charcoal or alumina, palladium being preferred. This metal may also be combined with another such as silver, copper, gold, tellurium, zinc, chromium, molybdenum or thallium. These hydrogenation catalysts are known.

The catalyst may be present in any suitable form, for example in the form of a fluidized bed, or preferably as a fixed bed. The direction of flow may be upward or downward. The distribution of the catalyst within the catalyst bed may be designed so as to control the heat flows generated by the exothermic reaction. Thus, it is possible to regulate, for example, charge density, and porosity gradients of the catalyst in order to control the exothermicity of the reaction. For example, the first part of the catalyst bed may comprise less catalyst, while the second part may comprise more.

Stages for activating or regenerating the catalyst, in a known manner, may also be incorporated into the process. The co-feed of a dilution gas such as nitrogen or a recycled part of the product stream, preferably containing HFC-142, is also envisioned.

The hydrogenation stage is exothermic and therefore the reaction temperature may be controlled by means designed for this purpose in the reactor, if necessary. The temperature may vary by a few tens of degrees during the reaction. For example, the inlet temperature may range from 20° C. to 250° C., and the gain in temperature may range from 5° C. to 100° C.

The hydrogenation reaction is preferably carried out at an absolute pressure of between 0.1 and 20 bar and advantageously of between 1 and 5 bar.

The contact time (ratio between the volume of catalyst and the total charge flow) is generally between 0.1 and 100 seconds, preferably between 1 and 50 seconds and advantageously between 2 and 10 seconds.

The amount of hydrogen injected may vary within a wide range. The hydrogen/organics ratio may vary within a wide range, especially between 1 (the stoichiometric amount) and 50, preferably between 1.5 and 20, and advantageously between 3 and 15. A high ratio leads to dilution and thus to better management of reaction exothermicity.

According to one embodiment it is possible to control the exothermicity of the hydrogenation reaction while retaining a very good conversion and selectivity and/or to reduce the deactivation of the catalyst.

The process according to this embodiment is characterized in that (a) HCC-1122 is reacted in the gas phase with hydrogen in a superstoichiometric amount at a temperature of between 20 and 200° C., preferably of between 500 and 120° C., in the presence of a hydrogenation catalyst; (b) a portion of the gaseous output stream resulting from the reactor, comprising HCFC-142, unreacted hydrogen and optionally unreacted HCC-1122, is recycled and (c) HCFC-142 is recovered from the other portion of the gaseous output stream resulting from the reactor, optionally after a purification stage.

The gas stream comprising the recycling loop and the reactants can be preheated before introduction into the reactor. An adiabatic reactor is preferred.

At the end of the process involving stages (i) and (ii), the resultant HFC-142 can advantageously be purified.

The invention will now be further illustrated by the following non-limiting examples.

Example 1

Dehydrofluorination of 1,1,1-trifluoro-2-chloroethane (HCFC-133a)

The catalyst used was an $AlF_3$ catalyst prepared by fluorination of alumina in a fixed bed at about 280° C. using air and hydrogen fluoride (the volume concentration of acid in air being in the range from 5 to 10%). The catalyst has the following physicochemical characteristics:
form: beads which are 0.5-2 mm in diameter
BET surface area: 220 $m^2/g$
pore volume: 1.3 $cm^3/g$ A 250 $cm^3$ Inconel® reactor installed inside a furnace was charged with 10 g of the $AlF_3$ catalyst in the form of a fixed bed. The catalyst was dried under nitrogen at 250° C. and at atmospheric pressure. After one night, the temperature of the bed was increased at 500° C., nitrogen flow was reduced to zero and 1,1,1-trifluoro-2-chloroethane (HCFC-133a) was fed to the reactor with a contact time of 2 seconds. Conversion of 1,1,1-trifluoro-2-chloroethane (HCFC-133a) was approximately 45.0%. Selectivity for the desired (HCC-1122) product was approximately 93.0%.

Example 2

Hydrogenation of 1-chloro-2,2-difluoroethylene (HCC-1122)

A tubular reactor installed inside a furnace was charged with 10 g of a wet 0.5% Pd/C pellet type catalyst. The catalyst was first dried under nitrogen at 110° C. and at atmospheric pressure. Next the catalyst was reduced by introducing hydrogen into the nitrogen stream and maintaining the temperature at 110° C. After 2 hours, the temperature of the bed was decreased to 80° C., nitrogen flow was reduced to zero and 1-chloro-2,2-difluoroethylene (HCC-1122) was fed to the reactor. The molar ratio of hydrogen to the organic material was 8.7. The contact time was about 4.5 seconds. Conversion of 1-chloro-2,2-difluoroethylene (HCC-1122) was approximately 100.0%. Selectivity for the desired (HCFC-142) product was approximately 98.7%.

The invention claimed is:

1. A process for the preparation of 1-chloro-2,2-difluoroethane comprising the following stages:
    (i) dehydrofluorinating 1,1,1-trifluoro-2-chloroethane to form a first product stream comprising 1-chloro-2,2-difluoroethylene, and
    (ii) hydrogenating 1-chloro-2,2-difluoroethylene obtained in stage (i) to produce a second product stream comprising 1-chloro-2,2-difluoroethane.

2. The process according to claim 1 wherein stage (i) is carried out, in the liquid or gas phase, in the presence of a dehydrofluorinating agent or as a thermal decomposition.

3. The process according to claim 2 wherein the dehydrofluorinating agent is a base.

4. The process according to claim 3 wherein the base is an alkali or alkaline earth metal hydroxide.

5. The process according to claim 3, wherein the dehydrofluorinating agent is in a solid state, a molten state, or an aqueous or nonaqueous caustic solution.

6. The process according to claim 5 wherein a caustic solvent for the caustic solution is water.

7. The process according to claim 3 wherein stage (i) is conducted in the presence of a catalyst.

8. The process according to claim 1 wherein stage (i) is conducted at a temperature in a range from 20 to 300° C. in the absence of a catalyst.

9. The process according to claim 7 wherein stage (i) is conducted at a temperature in a range from 150 to 650° C.

10. The process according to claim 2 wherein stage (i) is a thermal decomposition, conducted at a temperature in a range from 350 to 1000° C. in the absence of a dehydrofluorinating agent.

11. The process according to claim 2, further comprising recovering the dehydrofluorinating agent after stage (i).

12. The process according to claim 1 wherein stage (ii) is conducted in the presence of a catalyst.

13. The process according to claim 1 wherein the 1-chloro-2,2-difluoroethylene obtained in stage (i) is diluted with an inert gas or by recycle of at least a part of the second product stream.

14. The process according to claim 1 wherein stage (ii) is conducted at an inlet temperature from 20° C. to 250° C.

15. The process according to claim 1, further comprising purifying 1-chloro-2,2-difluoroethane after stage (ii).

16. The process according to claim 1, further comprising separating 1-chloro-2,2-difluoroethylene from the first product stream after step (i).

* * * * *